(12) United States Patent
Cheng et al.

(10) Patent No.: US 8,580,319 B2
(45) Date of Patent: Nov. 12, 2013

(54) TOPICAL COMPOSITIONS COMPRISING FERMENTED EXTRACTS OF TRADITIONAL CHINESE MEDICINAL (TCM) INGREDIENTS, AND METHODS OF MAKING AND USING SAME

(75) Inventors: Jing Cheng, Shanghai (CN); Chia-Wen Chen, Eastchester, NY (US); Steven Francis Schnittger, Huntington, NY (US); Ming Lu, Shanghai (CN)

(73) Assignee: ELC Management, LLC, New York, NY (US)

( * ) Notice: Subject to any disclaimer, the term of this patent is extended or adjusted under 35 U.S.C. 154(b) by 0 days.

(21) Appl. No.: 13/270,529

(22) Filed: Oct. 11, 2011

(65) Prior Publication Data

US 2012/0328597 A1 Dec. 27, 2012

Related U.S. Application Data

(62) Division of application No. 12/713,959, filed on Feb. 26, 2010.

(60) Provisional application No. 61/159,272, filed on Mar. 11, 2009, provisional application No. 61/228,999, filed on Jul. 28, 2009.

(51) Int. Cl.
*A61K 36/00* (2006.01)

(52) U.S. Cl.
USPC .......................................................... 424/725

(58) Field of Classification Search
None
See application file for complete search history.

(56) References Cited

U.S. PATENT DOCUMENTS

| | | | |
|---|---|---|---|
| 4,677,152 A | 6/1987 | Allen et al. | |
| 4,702,844 A | 10/1987 | Flesher et al. | |
| 4,970,252 A | 11/1990 | Sakuta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz et al. | |
| 5,837,793 A | 11/1998 | Harashima et al. | |
| 5,846,397 A | 12/1998 | Manzatu et al. | |
| 6,139,855 A | 10/2000 | Cioca et al. | |
| 2006/0034875 A1 | 2/2006 | Nakanishi et al. | |
| 2006/0154261 A1 | 7/2006 | Saxon et al. | |
| 2006/0159714 A1 | 7/2006 | Thorel | |
| 2007/0292409 A1 | 12/2007 | Olefsky et al. | |
| 2009/0254572 A1 | 10/2009 | Redlich et al. | |
| 2010/0153016 A1 | 6/2010 | Stefanon et al. | |

FOREIGN PATENT DOCUMENTS

| | | | |
|---|---|---|---|
| CN | 1704451 A | * | 12/2005 |
| CN | 1970723 A | * | 5/2007 |
| JP | 61018708 | | 1/1986 |
| JP | 2001-151688 | | 6/2001 |
| JP | 2002212052 A | * | 7/2002 |
| JP | 2005179326 A | * | 7/2005 |
| KR | 2003-020908 A | | 3/2003 |
| KR | 2003020908 A | * | 3/2003 |
| KR | 2004083388 | | 10/2004 |
| KR | 2008094457 A | * | 10/2008 |
| RO | 88053 | | 7/1984 |
| RO | 88054 | | 7/1984 |
| WO | WO2004/024798 | | 3/2004 |
| WO | WO 2006-060475 | | 6/2006 |

OTHER PUBLICATIONS

Tian et al. World J Microbiol Biotechnol (2008) 24:861-866.*
Baxter, RA. Journal of Cosmetic Dermatology (2007) 7: 2-7.*
O'Shaughnessy, M. Chapter 4: Yin and Yang from "Traditional Chinese Medicine: Esthetician's Guide". Allured: Carol Stream, IL. 2008, pp. 15-19, pp. 15 and 17 in particular.*
O'shaughnessey, M. Traditional Chinese Medicine: Esthetician's Guide; Allured Publishing, Jan. 1, 2008. Tile page, Contents, Preface, 1-3, 15-25.
Gu et al., Antioxidant Activity of Natural and Cultured Cordyceps sp.; Zhongguo Zhong Yao Za Zhi, Jun. 2007; 32(11): 1028-1031; Abstract only.
Miller, Richard Alan: The Cordyceps Sinensis Medicinal Mushroom; A True Superfood; www.nexusmagazine.com; Nexu New Times; pp. 23-28; May-Jun. 2009.
http://www.lgcare.co.kr/english/news/news/news01.jsp?bid=91 &recno=84&searchnm=; LG Household & Health Care; News clipping and Press Release; Naturally Fermented Brand su:m 37 Launches; Jan. 2009.
PCT International Search Report; International Application No. PCT/US2010/025712; Completion Date: Sep. 29, 2010; Date of Mailing: Sep. 29, 2010.
PCT Written Opinion of the International Searching Authority, or The Declaration; International Application No. PCT/US2010/025712; Completion Date: Sep. 29, 2010; Date of Mailing: Sep. 29, 2010.
Derwent-Acc-No. 2000-266490; Dement-Week: 200023; Pertains to Japanese Publication No. JP2000072816; Publication Date: Mar. 7, 2000.

(Continued)

*Primary Examiner* — Amy L Clark
(74) *Attorney, Agent, or Firm* — Cynthia R. Miller

(57) ABSTRACT

The present invention relates to topical compositions containing fermented extracts of Traditional Chinese Medicinal (TCM) ingredients for improving the appearance and skin condition of the user. The topical compositions of the present invention are tailored for different users of different skin compositions according to TCM principles. The fermented TCM extracts are characterized by reduced odor and/or color in comparison with unfermented TCM extracts and are therefore more suitable for use in cosmetic products.

1 Claim, No Drawings

(56) References Cited

OTHER PUBLICATIONS

Derwent-Acc-No. 2007-748618; Derwent-Week: 200833; Pertains to Korean Publication No. KR2007031176; Publication Date: Mar. 19, 2007.
Derwent-Acc-No. 2008-D94241; Derwent-Week: 200828; Pertains to Korean Publication No. KR742502; Publication Date: Jul. 24, 2007.
Derwent-Acc-No. 2009-E77111; Derwent-Week: 200913; Pertains to Korean Publication No. KR2008094458; Publication Date: Oct. 23, 2008.
Wang, H., et al.; Biotransformation of piceid in Polygonum cuspidatum to resveratrol by Aspergillus oryzae; Appl. Microbiol Biotechnol (2007) 75:763-768.

* cited by examiner

TOPICAL COMPOSITIONS COMPRISING FERMENTED EXTRACTS OF TRADITIONAL CHINESE MEDICINAL (TCM) INGREDIENTS, AND METHODS OF MAKING AND USING SAME

CROSS-REFERENCE TO RELATED APPLICATIONS

This application is a divisional of U.S. Ser. No. 12/713,959, filed Feb. 26, 2010, which claims priority to U.S. Provisional Patent Application No. 61/159,272 filed Mar. 11, 2009 and U.S. Provisional Patent Application No. 61/228,999 filed Jul. 28, 2009.

FIELD OF THE INVENTION

The present invention relates to topical compositions for improving the appearance and skin condition of a user, while such topical compositions contain fermented extracts of Traditional Chinese Medicinal (TCM) ingredients with reduced color and odor. The present invention also relates to computer-based system and method for determining the skin composition of a specific user and selecting a suitable topical composition for such user based on his or her skin composition according to TCM principles.

BACKGROUND OF THE INVENTION

There is great interest in the cosmetic industry to develop products containing natural plant-derived materials that may be applied topically to the skin to provide anti-acne, anti-oil, and anti-cellulite benefits. Plant-based cosmetic products that enhance the appearance of skin are increasingly in demand. Active ingredients or components with skin care benefits can be obtained from either the entire plant or various parts of a plant, such as seeds, needles, leaves, roots, bark, cones, stems, rhizomes, callus cells, protoplasts, organs and organ systems, and meristems, either as dried powders or liquid extracts, which can then be incorporated into topical compositions.

Traditional Chinese Medicine (hereinafter "TCM") has been in existence for several thousands of years and is based largely on accumulated human experience in using naturally occurring plant and animal extracts to treat various diseases. In recently years, TCM practices have gained significant recognition by the Western world, especially for treatment of chronic pathological conditions. Certain TCM ingredients have been known to have skin care benefits for thousands of years, and cosmetic or skin care products containing such TCM ingredients are becoming more popular. Because the TCM ingredients are all natural, they are significantly more appealing to customers who are conscious of the side effects and adverse environmental impacts of synthetic compounds.

However, it is important to note that the basic principles of TCM are quite different from that of the western medicinal sciences. For example, TCM believes that an internal physiological balance has to be maintained for a person to be healthy, and all diseases are caused by one or more types of imbalances, and each type of imbalances manifests through an identifiable pattern of symptom and requires a particular set of treatments for correction. A TCM practitioner typically uses a compound prescription containing a blend of multiple herbal ingredients to treat various symptoms of a disease after careful examination of an individual patient, and such prescription is specifically designed for the patient to re-establish the internal physiological balance of such patient. In other words, the TCM practice takes an individualized treatment approach, instead of a "one-size-fits-all" treatment approach.

Unfortunately, the currently available skin care products containing naturally occurring TCM ingredients are mass-marketed to all consumers and fail to implement the individualized treatment approach of TCM. Therefore, it would be desirable to provide new cosmetic and skin care products containing TCM ingredients that adopt the individualized treatment approach of TCM in improving the appearance and skin condition of specific users.

Further, a problem commonly encountered when formulating TCM ingredients into cosmetic or skin care products is the distinctive color and undesirable odor associated with many TCM ingredients, which makes it difficult to form aesthically and olfactorily acceptable cosmetic or skin care compositions containing such TCM ingredients. It would also be desirable to process TCM ingredients by reducing the color and odor so that they can be readily formulated into aesthically and olfactorily acceptable cosmetic or skin care compositions.

SUMMARY OF THE INVENTION

The present invention provides topical compositions, each of which contains a unique blend of TCM ingredients specifically designed to improve the appearance and skin conditions of a particular sub-population of users characterized by a specific skin composition, according to the TCM principles. Specifically, one aspect of the present invention relates to a topical composition containing fermented extracts of *Cordyceps sinensis* mycelia, *Ginkgo biloba* leaf, *Polygonum cuspidatum* rhizome, and *Citrus reticulata* peel, which can be applied to the skin of a user with a balanced skin composition to improve the appearance and skin conditions of said user. Another aspect of the present invention relates to a topical composition containing fermented extracts of *Ganoderma lucidum* fruiting body, *Selaginella tamariscina* plant, *Ginkgo biloba* leaf, and *Calendula officinalis* flower, which can be applied to the skin of a user with a Yang-dominant or balanced-to-Yang skin composition to nourish Yin and restore the Yin-Yang balance in the skin. A further aspect of the present invention relates to a topical composition containing fermented extracts of *Rhodiola rosea* rhizome, *Perilla frutescens* fruit, *Phellodendron amurense* bark, and *Foeniculum vulgare* seed, which can be applied to the skin of a user with a Yin-dominant or balanced-to-Yin skin composition to nourish Yin and restore the Yin-Yang balance in the skin.

The present invention also provides a method for preparing a topical composition by first fermenting a blend of extracts from one or more TCM ingredients known to have undesirable odor and/or color in the presence of an aerobically metabolizing microorganism under suitable aerobic conditions for a period of time sufficient to reduce or eliminate the undesirable odor and/or color while preserving desirable biological activities of said TCM ingredients, and then formulating the fermented blend of TCM extracts into a cosmetically or pharmaceutically acceptable carrier to form said topical composition.

Further, the present invention provides a method for selecting a topical composition for a user to improve the appearance or skin condition of said user based on his or her skin composition, comprising: (a) collecting biological data from the user; (b) categorizing the skin composition of the user based on the collected biological data, wherein said categorization is indicative of the Yin-Yang balance of the skin or the lack thereof; and (c) selecting a topical composition for the user, wherein said topical composition contains a blend of fermented Chinese herbal extracts for maintaining or restoring the Yin-Yang balance of the skin. Preferably, the skin composition of the user is categorized by using a statistical model that weights the biological data according to TCM principles.

Other aspects and objectives of the present invention will become more apparent from the ensuring description, examples, and claims.

DETAILED DESCRIPTION OF THE INVENTION, AND PREFERRED EMBODIMENT THEREOF

The present invention provides several topical compositions, each of which contains a unique combination of fermented extracts of TCM ingredients for targeting a sub-population of users with a specific skin composition according to the TCM principles. In TCM practices, health is represented as a balance of Yin and Yang, which are opposing forces interconnected and interdependent in the natural world, giving rise to each other in turn. These two forces represent the bipolar manifestation of all things in nature, and because of this, one must be present to allow the other to exist. A constantly changing balance between Yin and Yang should be maintained within the body of a person. When one force is regularly dominating over the other, the health of the patient can become compromised, resulting in illness and disease. Therefore, when diagnosing a patient, TCM practitioners usually try to determine the exact nature of the Yin/Yang imbalance, and then correct it through the use of acupuncture, herbal remedies, exercise, diet and lifestyle. Once the balance is restored in the body, so is health.

Correspondingly, the topical compositions provided by the present invention are specifically designed for different sub-population of users with different skin compositions, which can be categorized according to the Yin and Yang balance/imbalance of the skin. For example, the skin compositions can be divided into three major categories: the Yin-Yang balanced skin composition (hereinafter referred to as "balanced skin composition"), the Yang-dominant skin composition, and the Yin-dominant skin composition. Additional categories can also be included to further quantify the degree of imbalance. For example, the skin composition categorization may further include a balance-to-Yang skin composition and a balance-to-Yin skin composition, which are relatively balanced skin compositions with slight Yang or Yin symptoms.

The specific skin composition of a patient can be determined by observing the skin condition, tongue color and tongue fur color of the patient (which are two important factors to be considered by TCM practitioners for diagnosis), as well as by gathering certain information from the patient regarding the person's age, bodily sensation, sleep pattern, and energy level. For example, the balanced skin composition is typically characterized by smooth, radiant, soft and delicate skin with good elasticity and even skin tone, and patients with the balanced skin composition usually also have lips and tongue of light red color with thin, pale white tongue fur color. The Yang-dominant skin composition is typically characterized by reddish cheek and red skin tone, oily skin surface, and tendency to develop allergy, acne, pigmentation, and premature wrinkles. Patients with the Yang-dominant skin composition may also have lips and tongue of bright red color with yellow tongue fur color, and they typically prefer cold drinks, become thirsty very easily, have bitter tastes in the mouth, often sweat when sleeping at night, easily irascible, and often suffer from internal heat. The Yin-dominant skin composition is typically characterized by pale skin tone, dry and easily desquamated skin with low water absorption and water retention capacity, and tendency to develop pigmentation and premature wrinkles Patients with the Yin-dominant skin composition may have pale or blue lips, light red or pale tongue color with white tongue fur color, and they typically prefer hot drinks, have relatively cold hands and feet, are sensitive to temperature decrease, and often feel tired or sleepy. Patients with balanced-to-Yang or balanced-to-Yin skin composition may exhibit similar symptoms as those with Yang-dominant or Yin-dominant skin composition but to a lesser degree.

Correspondingly, the present invention provides a method for selecting cosmetic or skin care products for users based on their specific skin compositions, by first collecting biological data (e.g., age, bodily sensation, sleep pattern, energy level, tongue color, tongue fur color, and skin condition of the user), then determining the skin composition of the user based on the collected biological data, and finally selecting a suitable cosmetic or skin care product for the user corresponding to his or her skin composition. Preferably, the biological data was collected by a preliminary facial examination of the user as well as requesting the user to fill out a questionnaire, and the data so collected is then processed by a computer-based system programmed with a statistical model for specifically for determining the skin compositions of a user by weighing the collected biological data according to TCM principles.

Unlike the Western medicinal science that typically uses one drug to treat one disease, the TCM practice adopts a compound or combinational approach in its herbal therapy, i.e., by using a blend of different herbal ingredients to target the root cause as well as different symptoms of the disease. A typical TCM formula contains four major ingredients, each playing its unique role while working together synergistically to achieve the optimal treatment results. The four major ingredients have been described in ancient texts as "emperor" or "king," "minister," "assistant" and "servant". This TCM philosophy models these four major ingredients components in a compound formula after a court of an emperor. The emperor or king ingredient serves as the principle in attacking the root cause of the disease; the minister ingredient acts to assist and augment the emperor or king ingredient; the assistant ingredient also assists the emperor or king ingredient, but it focuses on counter-reacting any possible side-effects of the emperor or king ingredient; and the servants ingredient acts to deliver the medicine where it should go. Sometimes, a single ingredient may perform double or triple duties in a single TCM herbal formula, e.g., both as the king and the minister, or as the king, the minister and the assistant, or the like. Correspondingly, the TCM herbal formula may have only 2 or 3 ingredients in total.

In the present invention, a blend of fermented plant extracts containing at least four, and preferably seven, ingredients is provided for users with a balanced skin composition to maintain and strengthen the balance between Yin and Yang in the patient's skin, improve the immune system and the skin barrier function of the patient, revitalize the skin, and enhance self-repair function of the skin. Such a blend contains fermented extracts from *Cordyceps sinensis* mycelia, *Ginkgo biloba* leaf, *Polygonum cuspidatum* rhizome, and *Citrus reticulata* peel. The *Cordyceps sinensis* mycelia extract functions as the emperor or king ingredient in this blend; the *Ginkgo biloba* leaf extract functions as the minister ingredient; the *Polygonum cuspidatum* rhizome extract functions as the assistant ingredient; and the *Citrus reticulata* peel extract functions as the servant ingredient. Preferably, this blend of fermented plant extract further comprises one or more additional minister ingredients selected from the group consisting of fermented extracts from *Poria cocos* sclerotium, *Panax ginseng* root, and *Perilla frutescens* fruit, and most preferably, it comprises all three additional minister ingredients.

The fermented extract of *Cordyceps sinensis* mycelia is preferably present in this blend at an amount ranging from about 10% to about 40%, more preferably from about 15% to about 35%, and most preferably from about 20% to about 30%, by total weight of the blend. The fermented extract of *Ginkgo biloba* leaf is preferably present in this blend at an amount ranging from about 2% to about 30%, more preferably from about 5% to about 20%, and most preferably from about 10% to about 15%, by total weight of the blend. The fermented extract of *Polygonum cuspidatum* rhizome is preferably present in this blend at an amount ranging from about 2% to about 30%, more preferably from about 5% to about 20%, and most preferably from about 10% to about 15%, by total weight of the blend. The fermented extract of *Citrus reticulata* peel is preferably present in this blend at an amount ranging from about 2% to about 30%, more preferably from about 5% to about 20%, and most preferably from about 10% to about 15%, by total weight of the blend. If present, the fermented extract of *Poria cocos* sclerotium is preferably at an amount ranging from about 10% to about 40%, more preferably from about 15% to about 35%, and most preferably from about 20% to about 30%, by total weight of the blend. If present, the fermented extract of *Panax ginseng* root is preferably at an amount ranging from about 0.1% to about 15%, more preferably from about 1% to about 10%, and most preferably from about 3% to about 5%, by total weight of the blend. If present, the *Perilla frutescens* fruit is preferably at an amount ranging from about 2% to about 30%, more preferably from about 5% to about 20%, and most preferably from about 10% to about 15%, by total weight of the blend.

For users with a Yang-dominant or balanced-to-Yang skin composition, the present invention provides a blend of fermented plant extracts containing at least four, and preferably seven, ingredients to nourish the Yin energy in the skin, balance/neutralize the excess Yang energy, promote metabolism in the skin, facilitate circulation of bodily fluid as well as transportation of any turbid Qi (which is believed to be the cause of various diseases in TCM theories), regulate the immune system, improve the skin barrier function, and enhance the self-repair function of the skin. Such a blend contains fermented extracts from *Ganoderma lucidum* fruiting body, *Selaginella tamariscina* plant, *Ginkgo biloba* leaf, and *Calendula officinalis* flower. The *Ganoderma lucidum* fruiting body extract functions as the emperor or king ingredient in this blend; the *Selaginella tamariscina* plant functions as the minister ingredient; the *Ginkgo biloba* leaf extract functions as the assistant ingredient; and the *Calendula officinalis* flower extract functions as the servant ingredient. Preferably, this blend of fermented plant extract further comprises one or more additional minister ingredients selected from the group consisting of fermented extracts from *Centella asiatica* plant, *Scutellaria baicalensis* root, and *Polygonum cuspidatum* rhizome, and most preferably, it comprises all three additional minister ingredients.

The fermented extract of *Ganoderma lucidum* fruiting body is preferably present in this blend at an amount ranging from about 10% to about 45%, more preferably from about 15% to about 40%, and most preferably from about 20% to about 30%, by total weight of the blend. The fermented extract of *Selaginella tamariscina* plant is preferably present in this blend at an amount ranging from about 2% to about 35%, more preferably from about 5% to about 25%, and most preferably from about 10% to about 15%, by total weight of the blend. The fermented extract of *Ginkgo biloba* leaf is preferably present in this blend at an amount ranging from about 0.1% to about 20%, more preferably from about 1% to about 15%, and most preferably from about 3% to about 10%, by total weight of the blend. The fermented extract of *Calendula officinalis* flower is preferably present in this blend at an amount ranging from about 2% to about 35%, more preferably from about 5% to about 25%, and most preferably from about 10% to about 15%, by total weight of the blend. If present, the fermented extract of *Centella asiatica* plant is preferably at an amount ranging from about 2% to about 35%, more preferably from about 5% to about 25%, and most preferably from about 10% to about 15%, by total weight of the blend. If present, the fermented extract of *Scutellaria baicalensis* root is preferably at an amount ranging from about 2% to about 35%, more preferably from about 5% to about 25%, and most preferably from about 10% to about 15%, by total weight of the blend. If present, the *Polygonum cuspidatum* rhizome is preferably at an amount ranging from about 2% to about 35%, more preferably from about 5% to about 25%, and most preferably from about 10% to about 15%, by total weight of the blend. This blend of fermented plant extracts is used to balance both the Yang-dominant skin composition and the balanced-to-Yang skin composition, but at different concentrations. For example, the concentrations of fermented plant extracts in products designated for the balanced-to-Yang skin composition are preferably from 25% to 75%, more preferably from about 40% to about 60%, of those in products designated for the Yang-dominant skin composition.

For users with a Yin-dominant or balanced-to-Yin skin composition, the present invention provides a blend of fermented plant extracts containing at least four, and preferably seven, ingredients to nourish the Yang energy in the skin, balance/neutralize the excess Yin energy, strengthen the body fluid circulation, improve the immune system, enhance the skin barrier function, and enhance the self-repair function of the skin. Such a blend contains fermented extracts from *Rhodiola rosea* rhizome, *Perilla frutescens* fruit, *Phellodendron amurense* bark, and *Foeniculum vulgare* seed. The *Rhodiola rosea* rhizome extract functions as the emperor or king ingredient in this blend; the *Perilla frutescens* fruit functions as the minister ingredient; the *Phellodendron amurense* bark extract functions as the assistant ingredient; and the *Foeniculum vulgare* seed extract functions as the servant ingredient. Preferably, this blend of fermented plant extract further comprises one or more additional minister ingredients selected from the group consisting of fermented extracts from *Santalum album* stem, *Hordeum distichon* seed, and *Citrus reticulata* peel, and most preferably, it comprises all three additional minister ingredients.

The fermented extract of *Rhodiola rosea* rhizome is preferably present in this blend at an amount ranging from about 10% to about 50%, more preferably from about 15% to about 45%, and most preferably from about 25% to about 30%, by total weight of the blend. The fermented extract of *Perilla frutescens* fruit is preferably present in this blend at an amount ranging from about 0.5% to about 30%, more preferably from about 1% to about 20%, and most preferably from about 5% to about 15%, by total weight of the blend. The fermented extract of *Phellodendron amurense* bark is preferably present in this blend at an amount ranging from about 0.5% to about 30%, more preferably from about 1% to about 20%, and most preferably from about 5% to about 15%, by total weight of the blend. The fermented extract of *Foeniculum vulgare* seed is preferably present in this blend at an amount ranging from about 0.1% to about 15%, more preferably from about 1% to about 10%, and most preferably from about 2% to about 5%, by total weight of the blend. If present, the fermented extract of *Santalum album* stem is preferably at an amount ranging from about 0.1% to about 15%, more preferably from about 1% to about 10%, and most preferably from about 2% to about 5%, by total weight of the blend. If present, the fermented extract of *Hordeum distichon* seed is preferably at an amount ranging from about 10% to about 50%, more preferably from about 15% to about 45%, and most preferably from about 25% to about 30%, by total weight of the blend. If present, the *Citrus reticulata* peel is preferably at an amount ranging from about 5% to about 40%, more preferably from about 10% to about 30%, and most preferably from about 15% to about 20%, by total weight of the blend. This blend of fermented plant extracts is used to balance both the Yin-dominant skin composition and the balanced-to-Yin skin composition, but at different concentrations. For example, the concentrations of fermented plant extracts in products designated for the balanced-to-Yin skin composition are preferably from 25% to 75%, more preferably from about 40% to about 60%, of those in products designated for the Yin-dominant skin composition.

The present invention further provides a blend of fermented plant extracts for treating dark circles, puffiness, and wrinkles around the periorbital areas. According to TCM theories, dark circles are caused by stasis of Qi and body fluid, while puffiness around the eye area is caused by dampness and stasis of body fluid. Therefore, the present invention provides a blend of fermented plant extracts containing four ingredients for complementing Qi, improving the circulation of body fluid, removing dampness, tightening the skin, and prevent pre-mature skin aging. Such a blend contains fermented extracts from *Ligusticum chuangxiong* root, *Paeonia lactiflora* root, *Rehmannia glutinosa* root, and *Zizyphus jujube* fruit. The *Ligusticum chuangxiong* root extract functions as the emperor or king ingredient in this blend; the *Paeonia lactiflora* root functions as the minister ingredient; the *Rehmannia glutinosa* root extract functions as the assistant ingredient; and the *Zizyphus jujube* fruit extract functions as the servant ingredient. The fermented extract of *Ligusticum chuangxiong* root is preferably present in this blend at an amount ranging from about 5% to about 50%, more preferably from about 10% to about 40%, and most preferably from about 20% to about 30%, by total weight of the blend. The fermented extract of *Paeonia lactiflora* root is preferably present in this blend at an amount ranging from about 5% to about 50%, more preferably from about 10% to about 40%, and most preferably from about 20% to about 30%, by total weight of the blend. The fermented extract of *Rehmannia glutinosa* root is preferably present in this blend at an amount ranging from about 5% to about 50%, more preferably from about 10% to about 40%, and most preferably from about 20% to about 30%, by total weight of the blend. The fermented extract of *Zizyphus jujube* fruit is preferably present in this blend at an amount ranging from about 5% to about 50%, more preferably from about 10% to about 40%, and most preferably from about 20% to about 30%, by total weight of the blend.

The above-described blends of plant extracts can further include other plant extracts of known skin care benefit but are not specifically mentioned herein. Such plant extracts may include, but are not limited to, those obtained from roots, leaves, flowers, stalks or other parts of plants such as *Simmondsia Chinensis, Camellia Sinensis, Coffee Arabica, Betula Alba, Zea Mays, Siegesbeckia Orientalis, Helianthus Annus, Hordeum Vulgare, Cucumis Sativus, Carthamus Tinctorius, Mangifera Indicia, Garcinia Indica, Anthemus Nobilis, Arabidopsis Thaliana, Myrtus Communis, Apium Graveolens* (Celery), *Arabidopsis Thaliana, Padina Pavonica, Beta Vulgaris, Betula Alba, Butyrosperum Parkii, Garcinia Mangostana, Racemusus, Platycodon, Emblica Officinalis, Criste Marine, Lavande Papillon, Polygonum Cuspidatum, Laminaria Japonica, Fucus Vesiculosis, Borago Officinalis, Phyllanthus Emblica, Inonotus Obliquus, Calophyllum Inophyllum, Scutellaria Baicalensi*), *Boswellia Serrata, Boswellia Bhau-dajiana, Boswellia Frereana, Boswellia Papyrifera, Sudanese Boswellia Sacra, Boswellia Carteri, Commiphora Incisa, Commiphora Myrrha, Commiphora Abyssinica, Commiphora Erthraea, Commiphora Molmol, Bursera Microphylla; Nidularium Procerumt, Curcuma Longa, Macrycystis Pyrifera, Pleurotus Ostreatus, Hypsizygus Ulmarius, Cladosiphon Okamuranus, Acalypha Wilkesiana, Acanthopanax Gracilistylus, Allium Sativum, Ananus Comosus, Cissampelos Sympodialis, Coriolus Versicolor, Echinacea Purpurea, Grifola Frondosa, Harpagophytum Procumbens, Panax Ginseng, Polygala Tenuifolia, Poria Cocos, Silybum Marianum, Smilax Glabra, Tinospora Cordifolia, Uncaria Tomentosa, Withania Somnifera, Echinancea, Viscum Album, Capparis Moonii, Capsella Brusa Pastoris, Doliocarpus Verruculosus, Kaempferia Galanga, Sauropus Androgynus, Tetracapidium Conophorum, Pinus Pinaster, Vitis Vinefera, Pluchea Indica, Viola Hondoensis, Triphala Chebula, Citri Reticulatae, Tepescohuite, Mimosa Pudica, Silymarin, Eucommia, Menyanthes Trifoliata, Calluna Vulgaris, Rosa Canina, Polyporus Umbellatus, Chamomilla Recutita, Pygeum Africanum, Actina Boswellia, Soft Pygeurm Capsicum Annum, Carpinus Laxiflora, Parinus Tschonoskii, Castanopsis Cuspidata, Selaginella Tamariscina, Rosmarinus Officinalis, Cayaponia Tayuya, Celosia, Cristata, Cercis Chinensis, Haplophyllum hispanicum, Scutellaria Rivularis, Centauriumt, Polygonum Cuspidatum, Nigella Sativa, Rhodiola Rosea, Anemarrhena asphodeloides, Zhi Mu, Uncaria Tomentosa Cereus Granidflora, Chaenomeles Sinensis, Lyngbya, Viapure Poria, Polyporus Umbellatus, Chrysanthellum Indicum, Tridentata marginate, Paeonia Albiflora, Saussurea Costus, Saussurea Lappa, Magnolia Officianalis, Echineacea Pallida* and those set forth on pages 2755-2757 of the C.T.F.A. International Cosmetic Ingredient Dictionary and Handbook, Eleventh Edition, 2006, which is hereby incorporated by reference in its entirety.

Particularly, extracts from certain fungi with known medicinal benefits can be included in the blends of plant extracts of the present invention. For example, fungi from the genus *Trametes* are known for their medicinal properties. Sophisticated outdoorsmen will sometimes chew a piece of fungi picked from *Trametes Versicolor* (also referred to as Turkey Tail) like gum when they are hiking in the woods. It has been discovered by the inventors that in addition to their known medicinal properties, *Trametes* extracts also have beneficial properties when applied to the skin. Specifically, *Trametes* extracts contain certain chemical components that are particularly effective in whitening or brightening the skin. It is believed that such skin-whitening or brightening effect is achieved either through inhibition of tyrosinase activity or other cellular pathways that lead to skin pigmentation, thereby preventing formation of age spots or mottled skin, or through destruction of melanin in already formed age spots or mottled skin and thereby improving the overall evenness of the skin tone. Extracts from the *Trametes* genus are also excellent moisturizers, and some species may also be useful in absorbing excess sebum in oily skinned individuals.

Various plants or raw plant materials as described hereinabove are first cut and cleaned and then subjected to a low temperature water extraction process, in which the plant materials are immersed in a solvent system consisting essentially of deionized water at a temperature ranging from about 75° C. to about 95° C. (preferably from about 80° C. to about 90° C.) and a pressure ranging from about 0.03 to about 0.05 mpa for a duration of about 8 to 10 hours. The extraction solution is then concentrated at a temperature ranging from about 50° C. to about 65° C. (preferably from about 55° C. to about 60° C.) and under a vacuum condition characterized by a negative pressure ranging from about 1 torr to about 100 torr, more preferably from about 5 torr to about 50 torr, and most preferably about 10-15 torr. The concentrated extract solution is then spray dried at a temperature ranging from about 100° C. to about 150° C., preferably 120° C. to about 140° C., to form fine powders ready for packaging and shipping.

The blends of plant extracts in the above-described fine powder form can be directly formulated into topical or cosmetic compositions. However, such topical or cosmetic compositions are typically characterized by a distinctive bitter odor and a brownish dark color commonly associated with TCM extracts and may not be considered aesthetically and olfactorily acceptable by most users of cosmetic or skin care products. In order to improve the aesthetic and olfactory appeal of the final cosmetic or skin care products, the present invention employs a unique fermentation process to further treat the blends of plant extracts as described hereinabove.

The fermentation process of the present invention comprises incubating a blend of plant extracts in the presence of yeast, fungi, or other suitable aerobically metabolizing microorganisms, under suitable aerobic conditions, for a period of time sufficient to reduce or eliminate the undesirable odor and/or color of the plant extracts while preserving the desirable biological activities of the TCM ingredients. In a particularly preferred embodiment, the microorganism used for fermenting the plant extracts is a fungus from the genus *Trametes*, and more preferably from the species *Trametes Versicolor*.

The fermentation process can take either one of two approaches. The first approach is a process in which the microorganism is fermented not only in the presence of the plant extracts but also with traditional culturing nutrients. During such incubation, the yeast or other microorganisms can multiply significantly in number. The second, and preferred, approach is to ferment the yeast or other microorganisms in an aqueous environment, in the presence of only the plant extracts and in substantial absence of any additional nutrients, or in a low nutrient media, so that during the fermentation process, the yeast or other microorganisms only engage in catabolic processing of the plant extracts. The incubation is monitored periodically for signs of the plateauing of biological activity, for example, a leveling off of pH, and then the system temperature is raised to between about 30-50° C., preferably about 40-45° C., for at least about 24 hours. In one embodiment, the temperature is then briefly raised to 90-95° C. for a period of about 5-10 minutes, which ruptures the yeast, releasing the cell contents. Alternately, the cells can be disrupted by sonication. The entire system is then cooled to room temperature, and filtered with progressively decreasing pore size to remove yeast debris, leaving a fermented extract that has significantly reduced odor and/or color in comparison with the unprocessed extract.

The amount of plant extracts used is also not critical; however, if it is desired to prevent proliferation of the yeast or other microorganisms, the amount should be controlled so as not to provide enough nutrients so to allow multiplication. Ordinarily, the amount of plant extracts used in the incubation medium of the present invention ranges from about 0.01 to about 10%, preferably from about 0.01 to about 5%, by total weight of the incubation medium, the concentration depending on the types of plant extracts used as well as on the solubility thereof.

In one embodiment of the invention as described above, the incubation medium contains simply water in addition to the plant extracts. In a preferred embodiment, the water used, however, is a structured water, i.e., I water, S water, or a combination of the two, as described, for example, in RO 88053 [S-type water], and RO 88054 (I-type water], and U.S. Pat. Nos. 5,846,397 and 6,139,855, the contents of which are incorporated herein by reference. The use of structured water in one or both of these phases of the fermentation process can further enhance the desired biological activities of the plant extracts. As also noted above, the incubation medium is generally not supplied with any other nutrients besides the plant extracts, so that the sole source of substrate for the microorganisms' biochemical activity is the plant extracts provided. However, in an alternate embodiment, the fermentation process can be performed in the presence of a nutrient medium appropriate for the growth of the microorganisms.

The fermentation process as described hereinabove not only functions to reduce or eliminate the undesirable odor and color typically associated with TCM ingredients, but is also capable of enhancing or boosting the desired biological activities of the TCM ingredients. Such desired biological activities include, but are not limited to: ATP-elevating activities, anti-inflammation activities, anti-irritation activities, immune modulating activities, blood circulation-enhancing activities, anti-oxidant activities, photoprotective activities, anti-histamine activities, skin-whitening activities, anti-chemotactic activities, collagen synthesis-enhancing activities, fibronectin synthesis-enhancing activities, anti-glycation activities, anti-phospholipase A2 (PLA2) activities, phosphodiesterase (PDE)-inhibiting activities, superoxide dismutase (SOD)-like activities, DNA synthesis-enhancing activities, protein synthesis-enhancing activities, DNA-repairing activities, skin barrier-repairing activities, anti-glycosaminoglycanase activities, anti-elastase activities, catalase-like activities, interlukin-1 (IL-1) alpha protein-inhibiting activities, interlukin-8 (IL-8) protein-inhibiting activities, prostaglandin E2 (PGE2)-inhibiting activities, cyclooxygenase-2 (COX-2)-inhibiting activities, anti-tyrosinase activities, anti-adhesion activities, 5-lipoxygenase (5-LO)-inhibiting activities, and the like.

The fermented blends of plant extracts as described hereinabove can be used for formulating various cosmetic and skin care compositions of various forms, such as anhydrous or aqueous gels, solutions or serums, emulsions (such as water-in-oil, oil-in-water, water-in-silicone, or silicone-in-water emulsions). Suggested amount of the fermented plant extracts as used in such compositions may range from about 0.001% to about 75%, preferably from about 0.05% to about 70%, more preferably from about 0.1% to about 65%. If in anhydrous form, the composition generally comprises from about 0.1-95% oil, and optionally other ingredients such as powders, sunscreens, and the like, with all percentages meaning percent by weight unless otherwise indicated. If in aqueous gel, solution, or serum form, the composition may comprise from about 1-99% water, and optionally other ingredients. If in emulsion form, the composition may comprise from about 0.1% to about 99%, preferably from about 5% to about 95%, more preferably from about 7% to about 90% water and from about 0.1% to 99%, preferably from about 5% to about 95%, more preferably from about 7% to about 90% oil or silicone.

Types of cosmetic or skin care compositions that the present invention covers include, but are not limited to: mascara, blush, eye shadow, eyeliner, skin cream, skin lotion, skin treatment serum, foundation, lipstick, lip gloss, and the like. Such compositions may include various cosmetic or skin care ingredients, as described hereinafter:

1. Oils

The cosmetic or skin care compositions of the present invention may contain one or more oils which may be volatile or non-volatile. The term "oil" refers to an ingredient that is pourable at room temperature (e.g. 25° C.) The term "volatile" means that the oil has a vapor pressure of greater than about 2 mm. of mercury at 20° C. Volatile oils may include silicones or paraffinic hydrocarbons. If present, such volatile oils may range from about 0.1 to 50%. Examples of volatile silicones include linear silicones such as hexamethyldisiloxane (0.5 centistokes (cs)), octamethyltrisiloxane (1.0 cs), decamethyltetrasiloxane (1.5 cs), dodecamethylpentasiloxane (2.0 cs); or cyclic volatile silicones generally referred to as "cyclomethicone", which may be octamethylcyclotetrasiloxane, decamethylcyclopentasiloxane, dodecamethylcyclohexasiloxane, and so on. Examples of volatile paraffinic hydrocarbons include isohexadecane, isododecane, C9-11 isoparaffins, and the like.

Nonvolatile oils may include silicones, hydrocarbons, or esters. The term "nonvolatile" means that the oil has a vapor pressure of less than about 2 mm. of mercury at 20° C. Examples of nonvolatile silicones include dimethicone or diethicone; phenyl-substituted silicones such as phenyl trimethicone, diphenyl dimethicone, phenyl dimethicone, trimethylsiloxyphenyl dimethicone, phenethyl dimethicone; and the like; C2-14 alkyl substituted silicones such as cetyl dimethicone, hexyl dimethicone, lauryl dimethicone; or fluorinated silicones such as perfluorononyl dimethicone, trifluoropropyl dimethicone; and the like.

Examples of non-volatile hydrocarbons include hydrocarbons having from 10 to 40 carbon atoms in the linear or branched form such as C10-40 isoparaffins, C12-20 isparaffins; or olefins having from about 18 to 54 carbon atoms, for example C18-26 olefin, C20-24 olefin, C26-54 olefin; polybutene, polyisobutene, polydecene, or hydrogenated derivatives thereof such as hydrogenated polyisobutene; isoeicosane; squalane; squalene; and so on.

Examples of esters include those formed by the reaction of mono-, di-, or polyhydric C1-10 alcohols with carboxylic acids having from about 1 to 40 carbon atoms, preferably fatty C6-22 carboxylic acids. Preferred alcohols include ethanol, propanol, butanol, hexanol, glycerin, and so on. Preferred carboxylic acids include myristic, stearic, isostearic, palmitic, behenic, and so on. One particularly preferred ester is formed by the reaction of a polyhydric alcohol with fatty carboxylic acids, more specification glycerin and stearic acid, to provide glyceryl stearate, diglyceryl diisostearate, glyceryl triisostearate, and so on. Most preferred is glyceryl stearate.

2. Film Formers

The cosmetic or skin care compositions of the present invention may comprise at least one film former which is capable of forming a film when applied to the skin surface. If present, suggested ranges of film former(s) are from about 0.1 to 45%, preferably from about 0.5 to 40%, more preferably from about 0.5 to 30%. Film formers may be synthetic or natural polymers. They may be water soluble or oil soluble. They may be in the form of particles in aqueous dispersion, or solubilized or dispersed in the lipophilic phase of the composition. Examples of film forming polymers include polyurethanes either in lipophilic form or in the form of particles in aqueous dispersion; copolymers from ethylenically unsaturated monomers, for example, homo- or copolymers of acrylates, ammonium acrylates, styrene, acrylamides, methacrylates, vinyl acetate, vinyl pyrrolidone; or siloxy silicate polymers such as trimethylsiloxysilicate, polymethylsilsesquioxane; or silicone gums which are general dimethicone or dimethiconol having a degree of polymerization ranging from about 100,000 to 100 million cs. Examples of such film forming polymers include, but are not limited to, acrylates copolymer, polyurethane, acrylamide/ammonium acrylate copolymer, acrylamides copolymer, acrylates/acrylamide copolymer, acrylates/ammonium methacrylate copolymer, acrylates/octylacrylamide copolymer, PVP, PVA, PVP/VA copolymer, acrylates/VA copolymer, acrylates/VP copolymer, ammonium styrene/acrylates copolymer, and so on. Also suitable are naturally occurring polymers such as shellac or cellulose. Preferred is where the film former is shellac in aqueous dispersion which comprises from about 10-70% water, 1-40% shellac, and optionally from about 0.1-40% of a monohydric alcohol (preferably isopropanol or ethanol) and from about 0.0001 to 10% of a neutralizer which may be ammonium hydroxide. Also preferred is where the film former comprises a vinyl pyrrolidone homo- or copolymer such as PVP, PVP/VA copolymer and so on.

3. Structuring Agents

The cosmetic or skin care compositions of the present invention may also contain at least one structuring agent which increases the viscosity or thickens the composition. If present, suggested ranges of structuring agent(s) are from about 0.1-70%, preferably from about 0.5-65%, more preferably from about 1-60%. Structuring agents may be natural or synthetic waxes, polymeric materials that increase viscosity, and the like. Examples of waxes include polyethylene, polypropylene, beeswax, beeswax modified by reacting with polyethylene glycol, such as PEG-8 beeswax, PEG-10 beeswax, carnauba, ceresin, microcrystalline, or fatty alcohols such as stearyl, behenyl; or fatty acids such as stearic acid, behenic acid, isostearic acid, and so on. Also suitable as structuring agents are polyamides or silicone polyamides. Examples include those sold by Arizona Chemical under the trademarks Sylvaclear® and Uniclear®, including those having the INCI names ethylenediamine/stearyl dimer tallate copolymer or ethylenediamine/stearyl dimer dilinolate copolymer, ethylenediamine/dimer tallate copolymer bis-hydrogenated tallow amide; Polyamide-3; ethylenediamine/hydrogenated dimer dilinoleate copolymer bis-di-C14-18 alkyl amide; Polyamide-4; bis-stearyl ethylenediamine/neopentyl glycol/stearyl hydrogenated dimer dilinoleate copolymer and the like. Silicone waxes may also be used including but not limited to stearyl dimethicone, behenyl dimethicone, behenoxy dimethicone, stearoxy dimethicone, and so on. Also suitable as structuring agents are N-acyl amino acids or esters or amides thereof; 12-hydroxystearic acid or esters or amides thereof; fatty acid esters of di- or trifunctional alcohol dimers; or alkylamides of di- or tricarboxylic acids. Examples include stearamide MEA-stearate, N-acyl glutamic acid diamide, and so on.

Also suitable as structuring agents are naturally occurring ingredients that increase viscosity such as gums, including but not limited to Acacia Senegal gum, Veegum (magnesium aluminum silicate), biosaccharide gum, *Boswellia Serrata* gum, *Cassia* gum, cellulose gum, *Gellan* gum, xanthan gum, algin, agarose, cellulose, hydroxyethylcellulose, and the like.

Silicone elastomers are also suitable structuring agents and include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

The cosmetic or skin care compositions of the present invention may also contain one or more aqueous phase thickeners. If present, suggested ranges are from about 0.1-30%, preferably from about 0.5-25%, more preferably from about 0.5-20%. Suitable thickeners include acrylic polymeric thickeners comprised of monomers of acrylic acid, methacrylic acid, or their simple $C_{1\text{-}22}$ alkyl esters. Acrylic polymer solutions include those sold by Seppic, Inc., under the tradename Capigel having the CTFA name Acrylates Copolymer.

Also suitable are acrylic polymeric thickeners that are copolymers of acrylic acid, methacrylic acid or their $C_{1\text{-}22}$ alkyl esters further copolymerized with one or more fatty alkoxylated alcohols. Examples of such thickening agents include acrylates/steareth-20 methacrylate copolymer, which is sold by Rohm & Haas under the tradename Acculyn 22, or acrylates/steareth-20/methacrylate crosspolymer which may be purchased from Rohm & Haas under the tradename Acculyn 88.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or CH$_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl(meth)acrylate, divinylbenzene, (poly) ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10\text{-}30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames.

Particularly suitable as the aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

Also suitable as aqueous phase thickening agents are various types of polysaccharides, such as xanthan gum, cellulose, dextrin, cyclodextrin, hydroxyethylcellulose, acacia gum, and the like.

4. Emulsifiers

The cosmetic or skin care compositions of the present invention may further comprise at least one emulsifier or surfactant. If present, suggested ranges of such emulsifier(s) or surfactant(s) are from about 0.01-40%, preferably from about 0.05-35%, more preferably from about 0.1-25%. Suitable emulsifiers may be silicone based emulsifiers or surfactants including linear or crosslinked polyoxyalkylene substituted organosiloxanes or alkyl substituted polyoxyalkylene organosiloxanes. Examples include those having the generic name dimethicone copolyol, cetyl dimethicone copolyol, and so on. Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000. Also suitable are ethoxylated propoxylated derivatives of $C_{6-30}$ saturated or unsaturated fatty acids, for example, Di-PPG-2 myreth-10 adipate, Di-PPG-2 Ceteth-4 adipate, Di-PPG Myristyl Ether Adipate, Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Most preferred for use in mascaras are organic emulsifiers that are the reaction product of polyethylene glycol with fatty acids, e.g. PEG1-200 with stearic, isostearic, myristic, behenic, cetearic, acids and so on. Particulately preferred is where the emulsifier comprises the reaction product of polyethylene glycol and stearic acid, e.g. PEG-100 stearate. Also suitable are derivatives of sorbitan such as Polysorbates; sorbitan esterified with stearic acid, e.g. sorbitan tristearate, and so on.

5. Particulates

The cosmetic or skin care compositions may further comprise particulates, either in the from of pigments, powders or mixtures. Suitable pigments include inorganic pigments or iron oxides that are red, yellow, or black. Also suitable are organic pigments that are FD&C or D&C colors or Lakes thereof such as yellows, reds, blues, etc. Suitable powders include titanium dioxide, mica, bismuth oxychloride, titanated mica, PTFE, silica, bentonite, kaolin, talc, and the like. If present, suggested ranges of pigments are from about 0.01-45%, preferably from about 0.05-35%. Suggested ranges of powders are from about 0.01-10%.

6. Humectants

The cosmetic or skin care compositions of the present invention may also contain one or more humectants. If present, suggested ranges of the humectant(s) are from about 0.1 to 25%. Humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, trehalose, and so on. Also suitable is urea or sugar derivatives, e.g. ethylhexylglycerin. In one preferred embodiment, the humectants used in the composition of the invention are $C_{1-6}$, preferably $C_{2-4}$ alkylene glycols, most particularly butylene glycol.

The compositions may further contain other ingredients including but not limited to preservatives, sunscreens, and so on.

The invention will be further described in connection with the following examples which are set forth for purposes of illustration only.

EXAMPLE 1

Fine powder containing a blend of plant extracts for maintaining and strengthening the Yin-Yang balance of a user with balanced skin composition was prepared according to the extraction and drying techniques described hereinabove, which contains:

| Ingredient | % by weight |
|---|---|
| Cordyceps sinensis mycelia | 24% |
| Ginkgo biloba leaf | 12% |
| Polygonum cuspidatum rhizome | 12% |
| Citrus reticulata peel | 12% |
| Poria cocos sclerotium | 24% |
| Panax ginseng root | 4% |
| Perilla frutescens fruit | 12% |
| Total | 100% |

EXAMPLE 2

Fine powder containing a blend of plant extracts for nourishing the Yin energy and balancing/neutralizing the excess Yang energy of a user with Yang-dominant skin composition was prepared according to the extraction and drying techniques described hereinabove, which contains:

| Ingredient | % by weight |
|---|---|
| Ganoderma lucidum fruiting body | 26.67% |
| Selaginella tamariscina plant | 13.33% |
| Ginkgo biloba leaf | 6.68% |
| Calendula officinalis flower | 13.33% |
| Centella asiatica plant | 13.33% |
| Scutellaria baicalensis root | 13.33% |
| Polygonum cuspidatum rhizome | 13.33% |
| Total | 100.00% |

EXAMPLE 3

Fine powder containing a blend of plant extracts for nourishing the Yang energy and balancing/neutralizing the excess Yin energy of a user with Yin-dominant skin composition was prepared according to the extraction and drying techniques described hereinabove, which contains:

| Ingredient | % by weight |
|---|---|
| Rhodiola rosea rhizome | 28.13% |
| Perilla frutescens fruit | 9.38% |
| Phellodendron amurense bark | 9.38% |
| Foeniculum vulgare seed | 3.13% |
| Santalum album stem | 3.13% |
| Hordeum distichon seed | 28.10% |
| Citrus reticulata peel | 18.75% |
| Total | 100.00% |

EXAMPLE 4

Fine powder containing a blend of plant extracts for treating dark circles, puffiness, and wrinkles around the eye areas of a user was prepared according to the extraction and drying techniques described hereinabove, which contains:

| Ingredient | % by weight |
|---|---|
| Ligusticum chuanxiong root | 25% |
| Paeonia lactiflora root | 25% |

-continued

| Ingredient | % by weight |
|---|---|
| *Rehmannia glutinosa* root | 25% |
| *Zizyphus jujube* fruit | 25% |
| Total | 100% |

EXAMPLE 5

A sterilized cultural medium containing an aqueous solution of Difco malt extract broth at 1.5 wt % or 15 grams/liter was inoculated with *Saccharomyces cerevisiae* (baker's yeast) at about 24° C. for about 14 hours, until the yeast reached the end of log phase growth, to form an inoculum. Fine powder containing a blend of plant extracts as described hereinabove in Examples 1-4 was then added into a New Brunswick Scientific Bioflo 6000 reactor/fermentor of about 100 liters in volume, together with the inoculum and various ingredients described at below:

| Ingredient | % by weight |
|---|---|
| De-ionized water | QS |
| Anti-foam | 0.01% |
| MEB | 1.37% |
| Inoculum | 1.00% |
| Powder containing TCM blend | 0.92% |
| Butylene glycol | 4.58% |
| Total | 100.00% |

The mixture was incubated at about 24° C. and mixed at a speed of about 200 rpm for about 4 hours. The ferment solution was then sequentially passed through a 1% Celite Hyflo gel (diamateous earth), an Ertel 5-micron cellulose pad, a Cell Flow Hollow Fiber PES 0.2-micron tangential flow filter (Spectrum Labs), and a SealKleen ultipore Nylon66 0.2-micron absolute dead-end filter (Pall Corporation).

EXAMPLE 6

Colors of the blends of plant extracts as described hereinabove in Examples 1-4 before and after the fermentation process of Example 5 were compared using a LICO 100 color meter (Paul N. Gardner Company). Specifically, the samples were filled into 11 mm ground glass cavettes and then placed in the color meter, which provided an automatic reading of the colors in Gardner Color Number, as follows:

| | Color | |
|---|---|---|
| Type of TCM Blend | Before Fermentation | After Fermentation |
| For Balanced Skin Composition | 8.3 | 8.1 |
| For Yang-Dominate Skin Composition | 6.1 | 5.5 |
| For Yin-Dominate Skin Composition | 9.4 | 9.2 |
| For Eyes | 6.0 | 5.6 |

All samples showed reduction in color after fermentation, in comparison with the same samples before fermentation.

EXAMPLE 7

Odors of the blends of plant extracts as described hereinabove in Examples 1-4 before and after the fermentation process of Example 5 were compared using an Alpha M.O.S. Fox electronic nose system. Specifically, a 1 mL aliquot of each sample was prepared in quadruplicate and ran on the electronic nose at about 45° C. and for about 250 or 450 seconds. The data obtained for each sample was plotted using the PSA model. In all cases, the PSA data showed observable difference between the TCM blends before fermentation and after fermentation. Further, smell tests conducted by human subjects confirmed a reduction of undesirable odor in TCM blends after fermentation, in comparison with the same blends before fermentation.

EXAMPLE 8

Five (5) different types of skin care serums were formulated with the fermented TCM extracts described hereinabove for users with different skin compositions, including balanced ("B"), Yang ("Ya"), balanced-to-Yang ("B-Ya"), Yin ("Yi"), and balanced-to-Yin ("B-Yi") skin compositions, respectively:

| | CONCENTRATION (WT %) | | | | |
|---|---|---|---|---|---|
| INGREDIENTS | B | Ya | B-Ya | Yi | B-Yi |
| De-ionized water | QS | QS | QS | QS | QS |
| *Cordyceps sinensis* mycelia extract (fermented) | 0.022 | — | — | — | — |
| *Ginkgo biloba* leaf extract (fermented) | 0.011 | 0.006 | 0.004 | — | — |
| *Polygonum cuspidatum* rhizome extract (fermented) | 0.061 | 0.012 | 0.009 | — | — |
| *Citrus reticulata* peel extract (fermented) | 0.011 | — | — | 0.017 | 0.013 |
| *Poria cocos* sclerotium extract (fermented) | 0.022 | — | — | — | — |
| *Panax ginseng* root extract (fermented) | 0.004 | — | — | 0.200 | 0.200 |
| *Perilla frutescens* fruit extract (fermented) | 0.041 | — | — | 0.008 | 0.006 |
| *Ganoderma lucidum* fruiting body extract (fermented) | — | 0.024 | 0.018 | — | — |
| *Selaginella tamariscina* plant extract (fermented) | — | 0.012 | 0.009 | — | — |
| *Calendula officinalis* flower extract (fermented) | — | 0.012 | 0.009 | — | — |
| *Centella asiatica* plant extract (fermented) | — | 0.012 | 0.009 | — | — |
| *Scutellaria baicalensis* root extract (fermented) | — | 0.012 | 0.009 | — | — |
| *Rhodiola rosea* rhizome extract (fermented) | — | — | — | 0.026 | 0.019 |
| *Phellodendron amurense* bark extract (fermented) | — | — | — | 0.008 | 0.006 |
| *Foeniculum vulgare* seed extract (fermented) | — | — | — | 0.003 | 0.002 |
| *Santalum album* stem extract (fermented) | — | — | — | 0.003 | 0.002 |

-continued

| INGREDIENTS | CONCENTRATION (WT %) | | | | |
| --- | --- | --- | --- | --- | --- |
| | B | Ya | B-Ya | Yi | B-Yi |
| *Hordeum distichon* seed extract (fermented) | — | — | — | 0.026 | 0.019 |
| Butylene glycol | 4.458 | 4.649 | 5.534 | 4.465 | 5.350 |
| Neopentyl glycol diheptanoate | 3.500 | 3.500 | 3.500 | 3.500 | 3.500 |
| Ethylhexyl isononanoate | 3.000 | 3.000 | 3.000 | 2.500 | 2.500 |
| PEG-60 hydrogenated castor oil | 1.800 | 1.800 | 1.800 | 1.800 | 1.800 |
| Pentylene glycol | 1.000 | 1.000 | — | 1.000 | — |
| Cetyl ethylhexanoate | 1.000 | 1.000 | 1.000 | 1.000 | 1.000 |
| Algae extract | 0.980 | 0.980 | 0.980 | 0.980 | 0.980 |
| Saccharomyces/xylinum black tea extract | 0.861 | 0.861 | 0.861 | 0.861 | 0.861 |
| Phenoxyethanol | 0.744 | 0.749 | 0.445 | 0.756 | 0.455 |
| Caprylyl glycol | 0.550 | 0.550 | 0.737 | 0.550 | 0.737 |
| Propylene glycol dicaprate | 0.549 | 0.549 | 0.549 | 0.549 | 0.549 |
| Dimethicone | 0.500 | 0.500 | 0.500 | — | — |
| Tromethamine | 0.420 | 0.420 | 0.381 | 0.462 | 0.419 |
| *Helianthus annuus* (sunflower) seedcake | 0.405 | 0.405 | 0.405 | 0.405 | 0.405 |
| Carbomer | 0.400 | 0.400 | 0.400 | 0.440 | 0.440 |
| Polyglyceryl-2 sesquiisostearate | 0.300 | 0.300 | 0.300 | 0.300 | 0.300 |
| Tocopheryl acetate | 0.200 | 0.200 | 0.200 | 0.200 | 0.200 |
| Behenyl alcohol | 0.200 | 0.200 | 0.200 | 0.100 | 0.100 |
| Malt extract | 0.153 | 0.165 | 0.120 | 0.153 | 0.118 |
| Glycerin | 0.120 | 0.120 | 0.120 | 0.120 | 0.120 |
| Disodium EDTA | 0.100 | 0.100 | 0.050 | 0.104 | 0.054 |
| *Inonotus obliquus* (mushroom) extract | 0.085 | 0.085 | 0.085 | 0.085 | 0.085 |
| Dextrin | 0.070 | — | — | — | — |
| Potassium sorbate | 0.051 | 0.051 | 0.051 | 0.051 | 0.051 |
| Xanthan gum | 0.050 | 0.050 | — | 0.050 | — |
| Aminopropyl ascorbyl phosphate | 0.050 | 0.050 | 0.050 | 0.050 | 0.050 |
| *Citrus grandis* (grapefruit) peel extract | 0.050 | — | — | — | — |
| Hordeum vulgare (barley) extract | 0.030 | 0.030 | 0.030 | 0.040 | 0.040 |
| Sodium hyaluronate | 0.020 | 0.020 | 0.100 | 0.020 | 0.100 |
| Hydroxyethylcellulose | 0.015 | 0.015 | 0.015 | 0.015 | 0.015 |
| Cellulose | 0.015 | 0.015 | 0.015 | 0.015 | 0.015 |
| Adenosine phosphate | 0.009 | 0.009 | 0.009 | 0.009 | 0.009 |
| Acetyl carnitine HCl | 0.009 | 0.009 | 0.009 | 0.009 | 0.009 |
| Creatine | 0.009 | 0.009 | 0.009 | 0.009 | 0.009 |
| Sodium citrate | 0.009 | 0.009 | 0.009 | 0.009 | 0.009 |
| *Cucumis sativus* (cucumber) fruit extract | 0.007 | 0.007 | 0.007 | 0.007 | 0.007 |
| Glycine soja (soybean) protein | 0.005 | 0.005 | 0.005 | 0.005 | 0.005 |
| Citric acid | 0.004 | 0.004 | 0.004 | 0.004 | 0.004 |
| Glycine | — | 0.500 | 0.050 | — | — |
| Phytic acid | — | 0.086 | 0.009 | — | — |
| Laminaria saccharina extract | — | 0.005 | 0.005 | — | — |
| *Oryza sativa* (rice) bran extract | — | 0.001 | — | — | — |
| Caffeine | — | — | 0.200 | — | 0.200 |
| Sodium mannose phosphate | — | — | — | 0.500 | 0.500 |
| Cholesterol | — | — | — | 0.200 | 0.200 |
| Linoleic acid | — | — | — | 0.200 | 0.200 |
| Squalane | — | — | — | 0.118 | 0.118 |
| Sodium RNA | — | — | — | 0.100 | 0.100 |
| *Triticum vulgare* (wheat) germ oil | — | — | — | 0.050 | 0.050 |
| *Helianthus annuus* (sunflower) seed oil | — | — | — | 0.020 | 0.020 |
| Sodium sulfite | — | — | — | 0.004 | 0.004 |
| Sodium metabisulfite | — | — | — | 0.004 | 0.004 |
| Sodium chloride | — | — | — | 0.001 | 0.001 |

EXAMPLE 9

Three (3) different types of watery lotions were formulated with the fermented TCM extracts described hereinabove for users with different skin compositions, including balanced ("B"), Yang ("Ya"), and Yin ("Yi") skin compositions, respectively:

| INGREDIENTS | CONCENTRATIONS (WT %) | | |
| --- | --- | --- | --- |
| | B | Ya | Yi |
| De-ionized water | QS | QS | QS |
| *Cordyceps sinensis* mycelia extract (fermented) | 0.011 | — | — |
| *Ginkgo biloba* leaf extract (fermented) | 0.005 | 0.003 | — |
| *Polygonum cuspidatum* rhizome extract (fermented) | 0.010 | 0.006 | — |
| *Citrus reticulata* peel extract (fermented) | 0.005 | — | 0.008 |
| *Poria cocos* sclerotium extract (fermented) | 0.011 | — | — |
| *Panax ginseng* root extract (fermented) | 0.002 | — | 0.200 |
| *Perilla frutescens* fruit extract (fermented) | 0.006 | — | 0.005 |
| *Ganoderma lucidum* fruiting body extract (fermented) | — | 0.012 | — |
| *Selaginella tamariscina* plant extract (fermented) | — | 0.006 | — |
| *Calendula officinalis* flower extract (fermented) | — | 0.006 | — |

-continued

| INGREDIENTS | CONCENTRATIONS (WT %) | | |
|---|---|---|---|
| | B | Ya | Yi |
| *Centella asiatica* plant extract (fermented) | — | 0.006 | — |
| *Scutellaria baicalensis* root extract (fermented) | — | 0.006 | — |
| *Rhodiola rosea* rhizome extract (fermented) | — | — | 0.013 |
| *Phellodendron amurense* bark extract (fermented) | — | — | 0.005 |
| *Foeniculum vulgare* seed extract (fermented) | — | — | 0.001 |
| *Santalum album* stem extract (fermented) | — | — | 0.001 |
| *Hordeum distichon* seed extract (fermented) | — | — | 0.013 |
| Ethanol | 6.000 | 6.000 | 6.000 |
| Butylene glycol | 5.229 | 5.420 | 3.236 |
| Trehalose | 1.400 | 1.400 | — |
| Glycerin | 1.120 | 1.120 | 0.120 |
| Polysorbate 20 | 1.000 | 0.800 | 0.800 |
| Pentylene glycol | 1.000 | 1.000 | 1.000 |
| Algae extract | 0.980 | 0.980 | 0.980 |
| Saccharomyces/xylinum black tea extract | 0.861 | 0.861 | 0.861 |
| Sodium citrate | 0.550 | 0.100 | 0.106 |
| Phenoxyethanol | 0.505 | 0.510 | 0.506 |
| Sodium mannose phosphate | 0.500 | 0.500 | 0.500 |
| Citric acid | 0.100 | 0.010 | 0.012 |
| Disodium EDTA | 0.100 | 0.100 | 0.100 |
| Ethylhexylglycerin | 0.100 | 0.100 | 0.100 |
| Xylitol | 0.100 | 0.100 | — |
| Dipotassium glycyrrhizate | 0.100 | 0.100 | 0.100 |
| *Inonotus obliquus* (mushroom) extract | 0.085 | 0.085 | 0.085 |
| Malt extract | 0.084 | 0.095 | 0.084 |
| Caprylyl glycol | 0.025 | 0.025 | 0.025 |
| Sodium hyaluronate | 0.020 | 0.020 | 0.020 |
| Hydroxyethylcellulose | 0.015 | 0.015 | 0.015 |
| Cellulose | 0.015 | 0.015 | 0.015 |
| Adenosine phosphate | 0.009 | 0.009 | 0.009 |
| Creatine | 0.009 | 0.009 | 0.009 |
| Acetyl carnitine HCl | 0.009 | 0.009 | 0.009 |
| *Glycine soja* (soybean) protein | 0.005 | 0.005 | 0.005 |
| Tocopheryl acetate | 0.001 | 0.001 | 0.001 |
| *Citrus grandis* (grapefruit) peel extract | 0.001 | — | — |
| Dextrin | 0.001 | — | — |
| Propylene glycol dicaprate | 0.001 | 0.001 | 0.001 |
| Glycine | — | 0.500 | — |
| Phytin acid | — | 0.086 | — |
| *Laminaria saccharina* extract | — | 0.005 | — |
| *Oryza sativa* (rice) bran extract | — | 0.001 | — |
| Dipropylene glycol | — | — | 1.000 |
| Sodium RNA | — | — | 0.100 |
| Sodium chloride | — | — | 0.001 |

EXAMPLE 10

An eye cream product was formulated with the fermented TCM extracts described hereinabove.

| INGREDIENTS | WT % |
|---|---|
| De-ionized water | QS |
| *Ligusticum chuanxiong* root extract (fermented) | 0.011 |
| *Paeonia lactiflora* root extract (fermented) | 0.011 |
| *Rehmannia glutinosa* root extract (fermented) | 0.011 |
| *Zizyphus jujube* fruit extract (fermented) | 0.011 |
| *Butyrospermum parkii* (shea butter) | 4.998 |
| Cetearyl alcohol | 4.240 |
| Butylene glycol | 4.229 |
| Hydrogenated polyisobutene | 3.500 |
| Phenyl trimethicone | 3.250 |
| Dimethicone | 2.150 |
| Polybutene | 2.000 |
| Polyglyceryl-3 beeswax | 2.000 |
| Polymethyl methacrylate | 1.724 |
| Isostearyl neopentanoate | 1.500 |
| Cetearyl glycoside | 1.060 |
| PEG-100 stearate | 1.000 |

-continued

| INGREDIENTS | WT % |
|---|---|
| Tocopheryl acetate | 1.000 |
| Polysilicone-11 | 0.800 |
| Phenoxyethanol | 0.632 |
| Propylene glycol dicaprate | 0.549 |
| Stearic acid | 0.500 |
| *Helianthus annuus* (sunflower) seedcake | 0.405 |
| Squalane | 0.375 |
| Glycerin | 0.350 |
| Methyl glucose sesquistearate | 0.350 |
| Ethylhexylglycerin | 0.298 |
| Mica | 0.294 |
| Caprylyl glycol | 0.245 |
| Titanium dioxide | 0.232 |
| Acrylates/C10-30 alkylacrylate crosspolymer | 0.200 |
| Phytosphingosine | 0.200 |
| *Gentiana lutea* (gentian) root extract | 0.198 |
| Aminomethyl propanol | 0.160 |
| Disodium EDTA | 0.150 |
| Yeast extract | 0.125 |
| *Hordeum vulgare* (barley) extract | 0.105 |
| Xanthan gum | 0.100 |
| *Camellia sinensis* (green tea) leaf extract | 0.100 |
| Linoleic acid | 0.100 |
| *Salvia officinalis* (sage) leaf extract | 0.100 |
| Sodium dehydroacetate | 0.100 |
| Sodium hyaluronate | 0.100 |
| Magnesium ascorbyl phosphate | 0.100 |
| Cholesterol | 0.100 |
| *Betula alba* (birch) extract | 0.100 |
| Malt extract | 0.069 |
| *Glycine soja* (soybean) protein | 0.050 |
| *Triticum vulgare* (wheat) germ extract | 0.050 |
| Hexylene glycol | 0.040 |
| Hydrogenated lecithin | 0.010 |
| *Cucumis sativus* (cucumber) fruit extract | 0.007 |
| Potassium sorbate | 0.002 |
| BHT | 0.001 |
| Tocopherol | 0.001 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claim is:

1. A topical composition for restoring Yin-Yang balance of skin of a person with Yang-dominant or balanced-to-Yang skin, said composition comprising an effective amount of a blend of fermented extracts of *Ganoderma lucidum* fruiting bodies, *Selaginella tamariscina* plants, *Ginkgo biloba* leaves, *Calendula officinalis* flowers, *Centella asiatica* plants, *Scutellaria baicalensis* root and *Polygonum cuspidatum* rhizome, wherein said blend of fermented extracts is obtained by:

(i) blending *Ganoderma lucidum* fruiting bodies, *Selaginella tamariscina* plants, *Ginkgo biloba* leaves, *Calendula officinalis* flowers, *Centella asiatica* plants, *Scutellaria baicalensis* root and *Polygonum cuspidatum* rhizome to provide a blend of extracts;

(ii) fermenting the blend of extracts with a microorganism, wherein the microorganism can be yeast cells, and culturing nutrients; or (iii) fermenting the blend of extracts with microorganisms, wherein the microorganisms can be yeast cells, in an aqueous environment in substantial absence of additional nutrients or low nutrient media to catabolically process the blend of extracts;

(iv) monitoring the fermentation of (ii) or (iii) for signs of plateauing biological activity;

(v) briefly raising the temperature to rupture the yeast cells to release yeast cell contents, or disrupting the yeast cells by sonication; and (vi) filtering to remove yeast cell debris and to recover the blend of fermented extracts, wherein the blend of fermented extracts has reduced odor and/or color, wherein the blend of fermented extracts is in the form of a fine powder, and wherein the topical composition further comprises a cosmetically or pharmaceutically acceptable carrier.

* * * * *